(12) United States Patent
Dean

(10) Patent No.: US 10,933,013 B1
(45) Date of Patent: Mar. 2, 2021

(54) ORAL HYGIENE COMPOSITIONS CONTAINING EXTRACT OF CANNABIS PLANT

(71) Applicant: Ethan D Dean, Kalkaska, MI (US)

(72) Inventor: Ethan D Dean, Kalkaska, MI (US)

(\*) Notice: Subject to any disclaimer, the term of this patent is extended or adjusted under 35 U.S.C. 154(b) by 468 days.

(21) Appl. No.: 15/495,286

(22) Filed: Apr. 24, 2017

Related U.S. Application Data

(60) Provisional application No. 62/327,224, filed on Apr. 25, 2016.

(51) Int. Cl.

| | |
|---|---|
| *A61K 8/97* | (2017.01) |
| *A61Q 11/00* | (2006.01) |
| *A61K 8/49* | (2006.01) |
| *A61K 8/34* | (2006.01) |
| *A61K 8/55* | (2006.01) |
| *A61K 8/19* | (2006.01) |
| *A61K 8/92* | (2006.01) |
| *A61K 36/185* | (2006.01) |

(52) U.S. Cl.
CPC .................. *A61K 8/97* (2013.01); *A61K 8/19* (2013.01); *A61K 8/34* (2013.01); *A61K 8/498* (2013.01); *A61K 8/553* (2013.01); *A61K 8/922* (2013.01); *A61Q 11/00* (2013.01); *A61K 2800/591* (2013.01)

(58) Field of Classification Search
None
See application file for complete search history.

(56) References Cited

U.S. PATENT DOCUMENTS

| | | |
|---|---|---|
| 6,403,126 B1 | 6/2002 | Webster et al. |
| 6,440,415 B1 * | 8/2002 | Johnson .................. A61K 8/046 424/125 |
| 8,895,078 B2 | 11/2014 | Mueller |
| 9,044,390 B1 | 6/2015 | Speier |
| 2004/0192760 A1 | 9/2004 | Whittle et al. |
| 2009/0196912 A1 | 8/2009 | Eickhoff et al. |
| 2015/0297653 A1 | 10/2015 | Speier |
| 2015/0297654 A1 | 10/2015 | Speier |
| 2016/0166498 A1 * | 6/2016 | Anastassov .............. A61K 8/19 424/52 |

FOREIGN PATENT DOCUMENTS

| | | |
|---|---|---|
| FR | 2973706 A1 | 10/2012 |
| WO | 2014058742 A1 | 4/2014 |

OTHER PUBLICATIONS

Turner, et al., Biomedical Mass Spectrometry, 7:247. (Year: 1980).*
Turner, et al., Journal of Natural Products, 43:169. (Year: 1980).*
Gottlieb, A., The Art and Science of Cooking with Cannabis, Ronin Publishing, Inc., Berkeley. (Year: 1993).*
Verhoeckx, et al., International Immunopharmacology, 6:656. (Year: 2006).*
Sarmento, et al., "Scientifically Sound Guidelines for THC in Food in Europe," nova-Institute. (Year: 2015).*
Bosy, et al., Journal of Analytical Toxicology, 24:562. (Year: 2011).*
European Patent Office, Espacenet, Bibliographic data: FR2973706 A1—Oct. 12, 2012 (2 pages).
European Patent Office, Patent Translate, FR2973706—Description and claims (12 pages).
Wikipedia—Cannabis Flower Essential Oil. https://en.wikipedia.org/wiki/Cannabis_flower_essential_oil#co . . . (6 pages).
International Highlife. A Beginners Guide to Understanding Terpenes in Cannabis. Your Guide to Terpens in Cannabis, by Seshata / Feb. 6, 2018. (8 pages).

\* cited by examiner

*Primary Examiner* — Michael Barker
(74) *Attorney, Agent, or Firm* — R. Reams Goodloe, Jr.

(57) ABSTRACT

Oral hygiene compositions including pharmacologically active ingredients extracted from one or more species of plants (or interbred strains thereof) in the *Cannabis* genus. In an embodiment, an extraction process may include techniques to maximize the ratio of tetrahydrocannabinolic acid ("THCA") to tetrahydrocannabinaol (THC) in the essential oil extract, in order to maximize the presence of the non-euphoric THCA. In an embodiment, a mouthwash composition is provided. In an embodiment, an essential oil extract may be applied neat. In an embodiment, an essential oil extract may be mixed with food grade carriers (e.g. glycerol, or vegetable oil) and/or diluents (e.g. water, ethanol), and used as mouth rinse, in a conventional rinse and spit fashion. In an embodiment, an essential oil extract may be mixed with food grade carries and/or diluents and used as an ingestible composition, in a rise and swallow fashion.

31 Claims, 1 Drawing Sheet

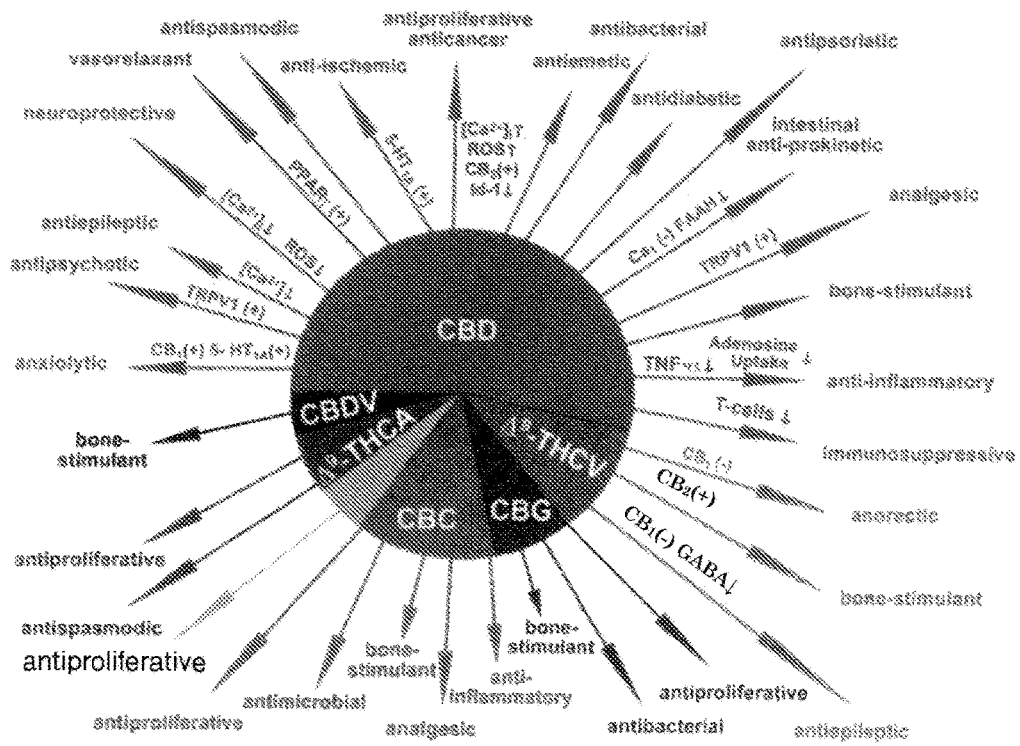

Pharmacological actions of non-psychotropic cannabinoids

Abbreviations: D 9 -THC, D 9 -tetrahydrocannabinol; D 8 -THC, D 8 -tetrahydrocannabinol; CBN, cannabinol; CBD, cannabidiol; D 9 -THCV, D 9 -tetrahydrocannabivarin; CBC, cannabichromene; CBG, cannabigerol; D 9 -THCA, D 9 -tetrahydrocannabinolic acid; CBDA, cannabidiolic acid; TRPV1, transient receptor potential vanilloid type 1; PPARg, peroxisome proliferator-activated receptor g; ROS, reactive oxygen species; 5-HT1A, 5-hydroxytryptamine receptor subtype 1A; FAAH, fatty acid amide hydrolase. (+), direct or indirect activation; ", increase; #, decrease.

ORAL HYGIENE COMPOSITIONS CONTAINING EXTRACT OF CANNABIS PLANT

RELATED PATENT APPLICATIONS

This application claims priority under 35 USC. § 119(e) from U.S. Provisional Patent Application Ser. No. 62/327,224 filed Apr. 25, 2016, entitled ORAL HYGIENE COMPOSITIONS CONTAINING EXTRACT OF *CANNABIS* PLANT, the disclosure of which is incorporated herein in its entirety, including the specification and claims, by this reference.

STATEMENT OF GOVERNMENT INTEREST

Not Applicable.

TECHNICAL FIELD

This disclosure relates to oral hygiene compositions, and particularly for mouthwash compositions to improve oral hygiene.

BACKGROUND

A continuing need exists for improvements in the prevention of tooth decay, in order to reduce the medical costs and personal pain and expense of visits to the dentist. Also, it would be advantageous if the growth of deposits of plaque and calcified plaque in humans were substantially reduced or eliminated by way of the regular use of a composition suitable for oral contact. In an embodiment, such compositions may be suitable for at least partial ingestion. Further, it would be advantageous if such improvements were available either in an easy to use formulation, or in the form of a substance which could be added to water and used after brushing of teeth.

Further, although I have uncovered various attempts at the use of an extract of *Cannabis* plant material in various pharmaceutical compositions, prior work specifically directed at the use of an extract of *Cannabis* plant material in mouthwashes per se seems elusive. One of the more comprehensive surveys of work in other somewhat related fields that I have uncovered is revealed in U.S. Pat. No. 9,044,390 B1, issued to Gary J. Speier on Jun. 2, 2015, and entitled Pharmaceutical Composition and Method of Manufacturing. The disclosure of that prior United States patent is incorporated herein in its entirety by this reference.

A common problem encountered by most humans is the need for periodic visits to the dentist in order to have teeth cleaned. That cleaning procedure may include the removal of plaque and calcified plaque. In order to reduce visits to the dentist, there thus remains a continuing unmet need for oral hygiene compositions which are helpful at prevention of plaque. And, it would be helpful to many consumers if new oral hygiene compositions were available that were effective at removal of plaque, tartar, and calcified plaque from teeth and adjacent gum tissues.

Some Objects, Advantages, and Novel Features

Accordingly, one objective is to provide oral hygiene compositions that include as an active ingredient essential extracts from *Cannabis* plant material, which compositions are suitable for use in mammals, and in particular, humans.

Another objective is to provide a process for the production of essential oils from *Cannabis* plant material which provides essential oils of extremely high purity and quality, as compared to prior art methods.

Yet another objective is to provide oral hygiene products which are available for ingestion, such as by way of lozenges, candy, chewing gum, or ingestible mouthwashes.

A related and important objective is to provide oral hygiene compositions which include extracts from *Cannabis* plants that are non-euphoric. In such embodiments, an objective may include the maximization of the use of tetrahydrocannabinolic acid ("THCA").

In an embodiment, a related and important objective is to provide a manufacturing process for oral hygiene products wherein essential oils are produced in a manner in which the decarboxylation of THCA is minimized, so as to minimize, if not eliminate, the presence of the related psychoactive compound, tetrahydrocannabinaol (THC).

A related and important objective is to provide oral hygiene compositions from which undesirable plant components, such as chlorophyll, as well as contaminants such as mold, mildew, fertilizers, and pesticides, have been almost entirely removed.

Finally, another important objective is to provide a high quality oral hygiene products which can be conveniently and easily manufactured using conventional manufacturing processes, so that manufacturing costs are minimized.

SUMMARY

I have now invented improved oral hygiene compositions including pharmacologically active ingredients extracted from one or more species of plants (or interbred strains thereof) in the *Cannabis* genus. In an embodiment, a mouthwash composition is provided. In an embodiment, an essential oil extract may be applied neat. In an embodiment, an essential oil extract may be mixed with food grade carriers and/or diluents and used as mouth rinse, in a conventional rinse and spit fashion. In an embodiment, an essential oil extract may be mixed with food grade carries and/or diluents and used as an ingestible composition, in a rise and swallow fashion. In yet other embodiments, an essential oil extract may be provided as an active ingredient in hard candy or lozenges.

DETAILED DESCRIPTION

This disclosure is directed to the manufacture and use of oral hygiene compositions utilizing extracts from the *Cannabis* plant genus. In an embodiment, a novel mouthwash composition may be provided utilizing non-euphoric constituents extracted from plant material from one or more species of plants in the Cannabaceae plant family, under room temperature and/or refrigerated extraction conditions. In an embodiment, a novel mouthwash composition may be provided utilizing extracts from the *Cannabis* plant genus which are extracted from plant material and processed under heated conditions.

As a first example, extracts as further described elsewhere herein may be obtained from *Cannabis sativa*, a herbaceous plant in the *Cannabis* genus, a species of the Cannabaceae plant family.

As a second example, extracts as further described elsewhere herein may be obtained from *Cannabis indica*, a herbaceous plant in the *Cannabis* genus, a species of the Cannabaceae plant family.

As a third example, extracts as further described elsewhere herein may be obtained from *Cannabis ruderalis*, a herbaceous plant in the *Cannabis* genus, an autoflowering plant, a species originating from central Russia.

My oral hygiene compositions may fall in to various categories, including mouthwashes, dentifrices, or lozenges.

In an embodiment, a mouthwash composition may be provided utilizing glycerin as a carrier, and one or more active ingredients including an extract from a selected plant species in the *Cannabis* genus. Optionally, mouthwash compositions may include solvents such as ethanol, or water, or co-solvents including ethanol and water. Final mouthwash solutions may include small amounts of colorings, flavorings, and other antibacterial or other conventional active ingredients. Such mouthwash compositions are anticipated to have both anti-plaque formation, and properties which enable removal of tartar, plaque, and/or calcified plaque.

A dentifrices compound may be provided which includes an insoluble dentally acceptable solid, which is utilized to physically and chemically clean the surface of the teeth. In an embodiment, the insoluble compound may comprise activated carbon particles. The dentifrices further include an extract from a selected plant species in the *Cannabis* genus. The dentifrices may be provided in a preparation which can be readily applied to a toothbrush, for example, via a viscous gel.

In order to provide suitable active ingredients for the oral hygiene compositions described herein, the active ingredients must be extracted from plant materials provided by one or more of the plant species noted above (or interbred strains therefrom). In an embodiment, extracts from *Cannabis* plants that are primarily if not essentially non-euphoric may be obtained by a cold extraction process as further described herein below. In an embodiment, extracts from *Cannabis* plants that are primarily if not essentially non-euphoric may be obtained as described in the U.S. Pat. No. 6,403,126 B1, which is incorporated herein in its entirety by this reference. In such non-euphoric mouthwash composition embodiments, an objective of the extraction process may include the maximization of tetrahydrocannabinolic acid ("THCA"). In such embodiments, an objective of the extraction process may include extracting compounds in a manner that the decarboxylation of THCA is minimized, so as to minimize if not substantially eliminate the presence of the related psychoactive compound, tetrahydrocannabinaol (THC). As the THC content will tend to rise as a result of drying or heating, utilizing freshly picked plant material will tend to maximize the production of the desirable THCA in such embodiments. Alternately, euphoric embodiments for a mouthwash composition may be provided, i.e., wherein activation has been effected such as by heating, and wherein more THC than THCA may be present in the final composition.

Since the tetrahydrocannabinaol (THC) is not activated (not decarboxylated) until it is heated, a suitable method for extraction of THCA may include solvent extraction under conditions of room temperature, or colder by direct contact between a carrier suitable for human ingestion and a first batch of *Cannabis* plant material from one or more of *Cannabis sativa*, or *Cannabis indica*, or *Cannabis ruderalis*, or interbred strains thereof. One suitable human ingestible solvent system includes glycerin as a carrier. In an embodiment, the carrier may have a composition that is almost all if not entirely of glycerin. In other embodiments, suitable human ingestible solvents in a solvent system may have a composition including vegetable oils, such as olive oil. In an embodiment, the carrier used in such a solvent system may be composed of almost all, if not entirely, of olive oil. To achieve extraction, contact is maintained between the first batch of plant material and the human ingestible solvent system under alternating temperature conditions. In an embodiment, the alternating temperature conditions may include (i) a selected time X at a refrigerated condition, and (ii) a selected time Y at a room temperature condition. Generally, the alternating temperature conditions may occur in a range of from about minus 20° F. to about 110° F. Or, in an embodiment, the alternating temperature conditions may occur in a range of from about minus 20° F. to about 90° F. In an embodiment, the method may include a refrigerated condition which is less than or equal to forty five degrees Fahrenheit (45° F.).

To maximize extraction of essential oils from the *Cannabis* plant material, a cycle of a refrigerated condition and a room temperature condition may be repeated for N+1 cycles, where N is a positive integer. In an embodiment, the repetitive refrigerated condition and the room temperature condition cycle are conducted over a period of time from about fifteen (15) days to about ninety (90) days. In such case, N would range from fourteen (14) to eighty nine (89). In an embodiment, the repetitive cycles of refrigeration and room temperature extraction may be conducted over time from about twenty five (25) days to about forty five (45) days. In an embodiment, the repetitive cycles of refrigeration and room temperature extraction may be conducted over a time of about thirty (30) days. In an embodiment, the extraction process may be initiated by extraction during refrigeration conditions. In an embodiment, the refrigerated condition may be maintained for a selected time X of approximately twelve (12) hours. In an embodiment, the room temperature condition may be maintained for a selected time Y of approximately twelve (12) hours. Once the extraction process has been completed, plant material is filtered from the solvent system, to produce a substantially pure liquid mouthwash composition. In various embodiments, the method of manufacture of a mouthwash composition may further comprise, either before or after extraction of target compounds from the *Cannibis* plant, as well as either before or after filtering of the extract, the additional step of aging said composition in sunlight, or equivalent artificial light, and decomposing plant material therein.

When room temperature or colder conditions are maintained during the extraction of essential oils from the *Cannabis* plant material, a mouthwash composition may be provided which is non-euphoric, or at least negligibly euphoric in chemical composition. As described above, in an embodiment, extraction may be performed utilizing direct extraction into a carrier such as glycerin, which is then directly utilized by the consumer. In such embodiments, the *Cannabis* extract is thus used directly, and is not handled or heated in a distillation or other purification process.

Alternately, batch processing may be utilized for the preparing high quality essential oil extracts. In such cases, repeated purification of a high quality essential *Cannabis* oil extract may involve heating and distillation of solvents in a solvent system from the essential oil extracts. First, a selected quantity of fresh plant material is provided. The selected plant material may be finely chopped or macerated in order to maximize the potential contact of plant material with solvent. In an embodiment, ethanol may be utilized as a selected solvent to extract active ingredients from the selected quantity of plant material. In an embodiment, I have found that the one or more solvents in a solvent system may include ethanol, either alone or in association with other solvents. In an embodiment, I have found that the one or more solvents in a solvent system may consist essentially of ethanol. In an embodiment, one or more of the solvents in a solvent system may include hexane. In an embodiment, one or more of the solvents in a solvent system may include isopropyl alcohol. In an embodiment, one or more of the solvents in a solvent system may include naptha. I have found that the one or more solvents may consist essentially of ethanol.

In order to prepare a mouthwash composition containing essential oil extracts from Cannabis plants, in an embodiment a method may include contacting a first batch of plant material from one or more of Cannabis sativa, or Cannabis indica, or Cannabis ruderalis, or interbred strains thereof, with one or more solvents in a solvent system. Contact is maintained between the first batch of plant material and the one or more solvents in the solvent system. In an embodiment, a contact time $T_1$ ranging from about two (2) minutes to as long as about thirty (30) days may be maintained. In various embodiments a contact time $T_1$ of about seventy two (72) hours, or of at least seventy two (72) hours and up to as much as thirty (30) days may be maintained, in order to provide a first batch of first level pregnant liquor solution. In an embodiment, a contact time $T_1$ in the range of from about four (4) hours to about twenty four (24) hours may be maintained. In an embodiment, a contact time $T_1$ in the range of from about (4) hours to about seventy two (72) hours may be maintained. In an embodiment, a contact time $T_1$ in the range of from about eight (8) hours to about twenty four (24) hours may be maintained. In an embodiment, a contact time $T_1$ in the range of from about twenty four (24) hours to about seventy two (72) hours may be maintained. In an embodiment, a contact time $T_1$ in the range of from about seventy two (72) hours to about seven (7) days may be maintained. In an embodiment, a contact time $T_1$ in the range of from about seven (7) days to about fourteen (14) days may be maintained.

Then, the one or more solvents are removed from the first pregnant liquor solution to provide a first batch of first level extract. The first level extract includes essential oils from the first batch of plant material.

In addition to processing a first batch of plant material as noted above, in an embodiment, I have found it useful to similarly process a second batch of plant material. Thus, a second batch of plant material from one or more of Cannabis sativa, or Cannabis indica, or Cannabis ruderalis, or interbred strains thereof, is contacted with one or more solvents in a solvent system. Contact is maintained between the second batch of plant material and the one or more solvents in the solvent system. In an embodiment, refrigerated conditions of about forty five degrees Fahrenheit (45° F.), or less, may be maintained. In an embodiment, refrigerated conditions of about thirty two degrees Fahrenheit (32° F.), or less, may be maintained. In an embodiment, a contact time $T_2$ of at least seventy two (72) hours may be selected, in order to provide a second batch of first level pregnant liquor.

Then, the one or more solvents are removed from the second batch of first level pregnant liquor solution, to provide a second batch of first level extract including the essential oils from the second batch of plant material. In various embodiments, the one or more solvents in a solvent system for the second batch of first level pregnant liquor solution may be the same as the solvent system utilized in processing the first batch of first level pregnant liquor solution. Alternately, different solvents may be utilized in a solvent system in the processing of different batches.

I have found that a higher purity essential oil extract may be obtained by combining the first batch of first level extract with the second batch of first level extract, and then further purifying the aforementioned combination, In an embodiment, such a method may include providing one or more solvents in a solvent system, and then combining the one or more solvents in the solvent system with the first batch of first level extract and with the second batch of first level extract to produce a first batch of second level pregnant liquor.

In order to remove impurities such as chlorophyll, I have found that mixing powdered activated carbon with the one or more solvents and the first batch and the second batch of first level extract is helpful. In this manner, the second level pregnant liquor initially comprises a liquid-solid mixture including activated carbon. In an embodiment, the amount of activated carbon added may be in the range of from about one (1) tablespoon (about 22 grams) to about five (5) tablespoons (about one hundred ten (110) grams) per one-half (½) gallon (about one point nine (1.9) liters) of second level pregnant liquor. I have also found that adding an agitation step, or multiple agitation steps over an adsorption time period $T_A$ such as in the range of from about three (3) to about fourteen (14) days, may be helpful. In an agitation step, the activated carbon may be thoroughly mixed with the second level pregnant liquor. In an embodiment, the adsorption time period $T_A$ may be about five (5) days.

When the selected adsorption time is completed, the activated carbon in the liquid-solid mixture in the second level pregnant liquor may be allowed to settle, to form a first supernatant layer and a first charcoal rich layer in the second level pregnant liquor. Then, the first supernatant layer is decanted from a first charcoal rich layer. In various embodiments, the second level pregnant liquor may be heated one or more times, or multiple times, before decanting. After decanting, the first supernatant layer may be cooled before further processing. Also, the first supernatant layer may be stored for a selected time period, during which gravity settling allows any remaining activated carbon or other solids to accrete and accumulate at the bottom of the processing container. This aids in purification of the extract, since waxes, lipids, and other contaminants attach to and/or settle with the activated charcoal. Upon completion of a settling process, a second supernatant layer may form in the container, above the precipitated solids.

Further, a high purity essential oil extract, for example as obtained in the manner just described in the preceding paragraph, may be heated, then gravity filtered, and the essential oil extract decanted, to leave residual solids contaminants at the bottom of a container.

The above noted steps may be repeated as appropriate to improve the quality of the essential oil extract by removing impurities therefrom. And, a filtration step, such as the use of filter paper or other suitable filtering medium, may also help separate the solids out of the remaining essential oil extract.

After removal of impurities, the one or more solvents are removed from the second supernatant layer (in a series of Z supernatant layers, Z being a positive integer, and wherein here Z=2, or such further supernatant layers Z in the event that additional processing is carried out). Thus, the first batch of second level pregnant liquor provides a first batch of second level extract comprising essential oils from said first batch and said second batch of plant material. Those of skill in the art will understand that Z steps will create Z supernatant layers, and thus process may be carried out through Z steps until a desired purity is attained for the essential oil extract.

Once a high purity essential oil extract has been obtained, that composition of matter may be utilized in a mouthwash composition. In various embodiments, a mouthwash composition may be provided wherein the essential oil extract comprises both tetrahydrocannabinaol (THC), and tetrahydrocannabinolic acid ("THCA"). In an embodiment, the decarboxylation of THCA may be minimized, so as to minimize if not substantially eliminate the presence of the related psychoactive compound, tetrahydrocannabinaol (THC), and in such embodiments the ratio of THCA to THC is greater than one (1). In other embodiments, activation of the THCA may be allowed to occur, such as by heating during processing, to allow the presence of the psychoactive compound tetrahydrocannabinaol (THC), and in such embodiments, the ratio of THCA to THC is less than one (1).

In an embodiment, an essential oil extract may be utilized neat, and directly applied to teeth and gums. In other embodiments, a mouthwash composition may be provided utilizing a carrier and an effective antiplaque amount of an essential oil extract from one or more of *Cannabis sativa*, or *Cannabis indica*, or *Cannabis ruderalis*, or interbred strains thereof. In an embodiment, it is believed advantageous to provide a wide variety of *cannabis* strains as constituents in an essential oil extract, so that a myriad of constituents may provide benefits. In various embodiments, a base composition which primarily includes a carrier and an effective anti-plaque amount of an essential oil extract in the range of from about one-quarter percent (0.25%) to about three percent (3.0%) by volume of the mouthwash composition.

In various embodiments, the selected carrier may include, or may consist essentially of glycerin. In various embodiments, the selected carrier may include, or may consist essentially of, edible oils. Suitable edible oils for use as a carrier include coconut oil, or olive oil.

In various embodiments, a mouthwash composition including a carrier and an effective anti-plaque amount of essential oil extract may be further diluted with a solvent. Suitable solvents include one or more of water and ethanol. In the case of ethanol, the mouthwash may include ethanol in a range from about zero point one percent (0.1%) to about forty percent (40%) by volume.

In various embodiments, a mouthwash composition may include an emulsifying agent. In some embodiments, a suitable emulsifying agent may include soy lecithin. In various embodiments, the soy lecithin may be present in the range from about zero point two five percent (0.25%) to about three percent (3.0%) by volume.

In an embodiment, the mouthwash may be converted to a dentifrice composition by addition of a selected amount of powdered activated carbon. In such an embodiment, the mouthwash may contain at least one suspending agent to assist in maintaining the solid activated carbon particles in a stable suspension. Such a mouthwash composition may have a mildly abrasive action on the teeth when rinsed around in the mouth, but in addition, the beneficial ability of the activated carbon to adsorb toxins is an improvement over current mouthwash formulations utilized by consumers.

In a method of use of the above described herbal marijuana extract mouthwash composition, such mouthwash may be utilized to remove dental plaque, and to remove tartar and clean gum tissue. The above described mouthwash may also be used to prevent plaque formation. It is anticipated that the above described mouthwash may reverse gingivitis, and rejuvenate receding gum tissue. Further, it is anticipated that the resinous properties of the essential oil extract may provide a protective coating that seals teeth, thus may be helpful preventing tooth decay.

Some mouthwash compositions which may be produced by solvent extraction of essential oils, and subsequent purification by removal of solvents by way of evaporation, distillation or the like, as may be understood according to description set forth herein and illustrated by the following Examples:

EXAMPLE 1. Five cups of glycerin (1183 ml) may be combined with 3 ml of essential oil extract and 2 tablespoons (29.6 ml) of soy lecithin. The active anti-plaque carrying component, the essential oil, thus comprises about 0.25% of the total volume.

EXAMPLE 2. Five cups of glycerin (1183 ml) may be combined with 3.5 ml of essential oil extract and 2 tablespoons (29.6 ml) of soy lecithin. The active anti-plaque carrying component, the essential oil, thus comprises about 0.29% of the total volume.

EXAMPLE 3. Five cups of glycerin (1183 ml) may be combined with 6 ml of essential oil extract and 2 tablespoons (29.6 ml) of soy lecithin. The active anti-plaque carrying component, the essential oil, thus comprises about 0.49% of the total volume.

EXAMPLE 4. Five cups of glycerin (1183 ml) may be combined with 12 ml of essential oil extract and 2 tablespoons (29.6 ml) of soy lecithin. The active anti-plaque carrying component, the essential oil, thus comprises about 0.98% of the total volume.

EXAMPLE 5. Five cups of glycerin (1183 ml) may be combined with 14 ml of essential oil extract and 2 tablespoons (29.6 ml) of soy lecithin. The active anti-plaque carrying component, the essential oil, thus comprises about 1.14% of the total volume.

EXAMPLE 6. Five cups of glycerin (1183 ml) may be combined with 24 ml of essential oil extract and 2 tablespoons (29.6 ml) of soy lecithin. The active anti-plaque carrying component, the essential oil, thus comprises about 1.94% of the total volume.

EXAMPLE 7. Five cups of glycerin (1183 ml) may be combined with 36 ml of essential oil extract and 2 tablespoons (29.6 ml) of soy lecithin. The active anti-plaque carrying component, the essential oil, thus comprises about 2.88% of the total volume.

In any of the examples, i.e. Example 1 through Example 7, the composition taught may be diluted with one or more solvents, such as water or ethanol. In the case of ethanol, the resulting final mouthwash composition may have an ethanol content of from about zero point one percent (0.1%) by volume, to about forty percent (40%) by volume.

Many pharmacological actions of non-psychotropic cannabinoids, (e.g., including efficacy as bone stimulants), and mechanisms of such action are known. For example, see: http://www.cmtlaboratory.com/wp-content/uploads/2014/12/Cannabinoid-Wheel-with-Description.pdf, the disclosure of which is incorporated herein by this reference. Such compounds may be present or omitted from various embodiments for mouthwash compositions, or in methods for production of *Cannabis* extracts suitable for use in such mouthwash compositions. Variations in *Cannabis* strains utilized, or variations in extraction methods, or in methods of purification of essential oil extracts, may result in use of more or less of various compounds. Such compounds include D9-THC, D9-tetrahydrocannabinol (D9-THC), D8-tetrahydrocannabinol (D8-THC), cannabinol (CBN), cannabidiol (CBD), D9-tetrahydrocannabivarin (D9-THCV), cannabichromene (CBC), cannabigerol (CBG), D9-tetrahydrocannabinolic acid (D9-THCA), cannabidolic acid (CBDA), transient receptor potential vanilloid type 1 (TRPV1), peroxisome proliferator-activated receptor g (PPARg), reactive oxygen species (ROS), 5-hydroxytryptamine receptor subtype 1A (5-HT1A), fatty acid amide hydrolase (FAAH).

It is to be appreciated that my oral hygiene compositions provide an appreciable improvement in the art of dental hygiene. My novel oral hygiene compositions address the widespread issue of plaque on teeth in mammals. It is believed that widespread adoption and use of the oral hygiene composition described and claimed herein may lead to a significant reduction in dental hygiene requirements, and the myriad of problems resulting from poor dental hygiene.

Although only a few exemplary embodiments have been described in detail, various details are sufficiently set forth in the specification provided herein to enable one of ordinary skill in the art to make and use the invention(s), which need not be further described by additional writing in this detailed description. It will be readily apparent to those skilled in the art that my mouthwash compositions, and processes for preparation of the same, may be modified from those embodiments provided herein, without materially departing from the novel teachings and advantages provided.

The aspects and embodiments described and claimed herein may be modified from those shown without materially departing from the novel teachings and advantages described herein, and may be embodied in other specific forms without departing from the spirit or essential characteristics thereof. Therefore, the embodiments presented herein are to be considered in all respects as illustrative and not restrictive. As such, this disclosure is intended to cover the processes and formulas described herein and equivalents thereof. Numerous modifications and variations are possible in light of the above teachings. It is therefore to be understood that within the scope of the appended claims, the invention(s) may be practiced otherwise than as specifically described herein. Thus, the scope of the invention(s), as set forth in the appended claims, and as indicated by the foregoing description, is intended to include variations from the embodiments provided which are nevertheless described by the broad interpretation and range properly afforded to the plain meaning of the claims set forth below.

The invention claimed is:

1. A mouthwash composition, comprising:
   (a) a carrier;
   (b) an effective calcified plaque removal amount of an essential oil extract from one or more of *Cannabis sativa*, or *Cannabis indica*, or *Cannabis ruderalis*, or interbred strains thereof,
   (c) wherein said effective calcified plaque removal amount of an essential oil extract is in a range of from about one-quarter percent (0.25%) to about three percent (3.0%) by volume of said mouthwash composition;
   (d) an emulsifying agent, the emulsifying agent comprising an amount effective to provide the mouthwash composition as an emulsion; and
   (e) wherein the effective amount of said essential oil extract is effective in removal of plaque and calcified plaque from teeth and adjacent gum tissues.

2. A method for preparing a mouthwash of claim 1 comprising extract from *Cannabis* plants, said method comprising:
   (a) contacting a first batch of plant material from one or more of *Cannabis sativa*, or *Cannabis* indica, or *Cannabis ruderalis*, or interbred strains thereof, with a human ingestible solvent system comprising glycerin;
   (b) maintaining contact between said first batch of plant material and said human ingestible solvent system under alternating temperature conditions, said alternating temperature conditions comprising (i) a selected time X at a refrigerated condition, and (ii) a selected time Y at a room temperature condition, said alternating temperature conditions having a range of from about minus 20° F. to about 110° F.;
   (c) repeating the refrigerated condition and the room temperature condition N+1 cycles, where N is a positive integer; and
   (d) filtering plant material from said solvent system, to produce a substantia pure liquid mouthwash composition comprising an extract from said plant material.

3. The method as set forth in claim 2, wherein said extract from *Cannabis* plants is present in an amount of from about fourteen point eight (14.8) milliliters (0.5 ounces) to about eighty eight point seven (88.7) milliliters (three (3) ounces) per one thousand one hundred eighty three (1183) milliliters (five (5) cups) of glycerin.

4. The method as set forth in claim 3, wherein said extract is present in an amount of from about fifty nine point one (59.1) milliliters (two (2) ounces) per one thousand one hundred eighty three (1183) milliliters (five (5) cups) of glycerin.

5. The method as set forth in claim 2, wherein said solvent system consists essentially of glycerin.

6. The method as set forth in claim 2, wherein said alternating temperature conditions starts with a refrigerated condition.

7. The method as set, forth in claim 2, wherein said refrigerated condition is less than or equal to forty five degrees Fahrenheit (45° F.).

8. The method as set forth in claim 2, wherein said alternating temperature conditions having a range of from about minus 20° F. to about 90° F.

9. The method as set forth in claim 2, wherein repeating the refrigerated condition and the room temperature condition N+1 cycles is conducted over time from about fifteen (15) days to about ninety (90) days.

10. The method as set forth in claim 9, wherein repetition of N+1 cycles is conducted over time from about twenty five (25) days to about forty five (45) days.

11. The method as set forth in claim 9, wherein repetition of N+1 cycles is conducted over a time of about thirty (30) days.

12. The method as set forth in claim 9, wherein said selected time X at said refrigerated condition is approximately twelve (12) hours.

13. The method as set forth in claim 9, wherein said selected time Y at said room temperature condition is approximately twelve (12) hours.

14. The method as set forth in claim 2, further comprising, either before or after filtering, an additional step of aging said composition in sunlight, or equivalent artificial light, and decomposing plant material therein.

15. A method for preparing a mouthwash of claim 1 comprising extract from *Cannabis* plants, said method comprising:
   (a) contacting a first batch of plant material from one or more of *Cannabis sativa*, or *Cannabis indica*, or *Cannabis ruderalis*, or interbred strains thereof, with a human ingestible solvent system comprising glycerin;
   (b) maintaining contact between said first batch of plant material and said human ingestible solvent system under alternating temperature conditions, said alternating temperature conditions comprising (i) a selected time of about twelve (12) hours at a refrigerated condition, and (ii) a selected time of about twelve (12) hours at a room temperature condition, said alternating temperature conditions having a range of from about minus 20° F. to about 110° F.;

(c) repeating the refrigerated condition and the room temperature condition N+1 cycles, where N is a positive integer, and wherein the number of cycles ranges from about twenty five (25) to about forty five (45);

(d) filtering plant material from said solvent system, to produce a substantially pure liquid mouthwash composition to produce a substantially pure liquid mouthwash composition comprising an extract from said plant material; and (e) either before filtering, or after filtering, or both, aging the liquid mouthwash composition in sunlight, or artificial light equivalent, and decomposing plant material remaining therein.

16. The method as set forth in claim 2, or in claim 15, wherein said extract from *Cannabis* plants consists essentially of non-euphoric compounds.

17. The method as set forth in claim 16, wherein said nom euphoric compounds comprise tetrahydrocannabinolic acid (THCA).

18. The mouthwash composition as set forth in claim 1, wherein said carrier comprises glycerin.

19. The mouthwash composition as set forth in claim 1, wherein said essential oil extract comprises tetrahydrocannabinolic acid (THCA).

20. The mouthwash composition as set forth in claim 1, wherein said essential oil extract consists essentially of tetrahydrocannabinolic acid (THCA).

21. The mouthwash composition as set forth in claim 18, wherein said essential oil extract comprises tetrahydrocannabinolic acid (THCA) and tetrahydrocannabinaol (THC), and wherein the ratio of THCA to THC is greater than one (1).

22. The mouthwash composition as set forth in claim 1, wherein said essential oil extract comprises tetrahydrocannabinolic acid (THCA) and tetrahydrocannabinaol (THC), and wherein the ratio of THCA to THC is less than one (1).

23. The mouthwash composition as set forth in claim 1, wherein said mouthwash composition further comprises ethanol in a range from about zero point one percent (0.1%) to about forty percent (40%) by volume.

24. The mouthwash composition as set forth in claim 1, or in claim 23, wherein said mouthwash composition further comprises water.

25. The mouthwash composition as set forth in claim 1, wherein said emulsifying agent comprises soy lecithin.

26. The mouthwash composition as set forth in claim 25, wherein said soy lecithin is present in a range of from about zero point two five percent (0.25%) to about three percent (3.0%) by volume.

27. The mouthwash composition as set, forth in claim 1, wherein said essential oil extract is obtained by the method of claim 1.

28. The mouthwash composition as set forth in claim 1, further comprising powdered activated carbon.

29. The mouthwash composition as set forth in claim 1, wherein said carrier comprises edible oil.

30. The mouthwash composition as set forth in claim 1, wherein said carrier comprises coconut oil.

31. The mouthwash composition as set forth in claim 1, wherein said carrier comprises olive oil.

* * * * *